United States Patent [19]

Edenbaum et al.

US005180632A

[11] Patent Number: 5,180,632

[45] Date of Patent: * Jan. 19, 1993

[54] ORTHOPEDIC CASTING MATERIAL HAVING REDUCED TACK AND REDUCED SLIP

[75] Inventors: Martin Edenbaum, Princeton Junction, N.J.; Kurt C. Frisch, Grosse Ile, Mich.; Aisa Sendijarevic, Troy, Mich.; Shaio-wen Wong, Claire Shores, Mich.

[73] Assignee: Carapace, Tulsa, Okla.

[*] Notice: The portion of the term of this patent subsequent to Oct. 29, 2008 has been disclaimed.

[21] Appl. No.: 452,217

[22] Filed: Dec. 18, 1989

[51] Int. Cl.⁵ .................. A61L 15/14; A61F 5/04; A61F 13/04; B32B 17/04
[52] U.S. Cl. .................................. 428/253; 428/254; 428/255; 428/273; 428/542.8; 428/913; 523/105; 602/5
[58] Field of Search ............... 428/253, 254, 255, 273, 428/542.8, 913; 128/90, 155, 156; 523/105

[56] References Cited

U.S. PATENT DOCUMENTS 4,667,661 5/1987 Scholz et al. .................... 128/90
5,061,555 10/1991 Edenbaum et al. .............. 428/253

Primary Examiner—George F. Lesmes
Assistant Examiner—James D. Withers
Attorney, Agent, or Firm—Woodcock Washburn Kurtz Mackiewicz & Norris

[57] ABSTRACT

Disclosed is an orthopedic casting material comprising a fabric coated or impregnated with a blend of polyisocyanate prepolymer and an effective detackifying quantity of one or more hydrophilic bisurethanes. In a preferred embodiment, the hydrophilic bisurethane is derived from the reaction of a polyethylene glycol having a molecular weight of about 4000 and methylene-4,4'-bis(phenylisocyanate) to form an isocyanate-terminated prepolymer which is then reacted with ethanol.

17 Claims, No Drawings

ORTHOPEDIC CASTING MATERIAL HAVING REDUCED TACK AND REDUCED SLIP

BACKGROUND OF THE INVENTION

This invention relates to an orthopedic casting material. More specifically, the invention relates to such casting materials which comprise fabric impregnated and/or coated with polyisocyanate prepolymer and which are treated with mineral oil and fluorocarbon polymer powder to reduce the tack, slip and foaming properties of the material during curing.

Most orthopedic casting tapes currently available are produced using curable resins coated on a substrate such as fiberglass, polyester or other synthetic or natural fabrics. For example, orthopedic casting tapes utilizing polyisocyanate prepolymers which react with water to initiate curing to polyurethanes are known. (U.S. Pat. No. 4,411,262 to von Bonin et al., U.S. Pat. No. 4,502,479 to Garwood et al.) Generally, the polyisocyanate prepolymer comprises the reaction product of an isocyanate and a polyol, which product polymerizes to polyurethane urea upon contact with water. The prepolymer-treated bandage is soaked in water prior to application to the body member, and the wet bandage is then applied to the body member. After the bandage is applied, the cast is smoothed with a gloved hand and held at certain points until it hardens. Since the resins in the bandage are quite tacky until they cure, the protective gloves worn by the cast applier tend to stick to the bandage. This is disadvantageous since it can lead to unwinding of the cast as layers of the tape pull apart from each other and the cast cannot be molded.

To alleviate the problem of "tackiness" in curable resin-coated bandages, Scholz et al. proposed, in U.S. Pat. No. 4,667,661, treating such bandages with certain lubricants to reduce the kinetic coefficient of friction of such sheets to less than about 1.2. The lubricant can be comprised of (a) hydrophilic groups which are covalently bonded to the curable resin, (b) an additive which is incompatible with the curable resin or (c) a combination of (a) and (b). As noted in the Scholz et al. patent (e.g., column 11, lines 21 et. seq.), the bandages treated with such lubricants become very slippery, and molding of the cast becomes easy due to the non-tacky nature of the resin. It is also noted in the Scholz et al. patent (column 8, lines 45-65) that materials such as mineral oil were evaluated as lubricants and, although they did give a non-tacky and even slippery feeling to the surface of the casting tape, which allowed easy application and moldability of the tape to the patient, the effect was transient. On average, Scholz et al. report, such materials lasted only a day to a week, apparently due to the dissolution of the oil into the resin.

There exists a need for a bandage material with improved handling properties, i.e., one which is neither too tacky nor too slippery.

SUMMARY OF THE INVENTION

It has now been found that such bandage materials can be obtained by blending with the polyisocyanate prepolymer utilized to coat the bandage material a hydrophilic bisurethane. More particularly, this invention relates to a prepolymer mixture for use in orthopedic casting materials comprising a polyisocyanate prepolymer and an effective detackifying quantity of one or more hydrophilic bisurethanes. This invention also relates to an orthopedic casting material comprising a fabric impregnated and/or coated with said prepolymer mixture.

DETAILED DESCRIPTION OF THE INVENTION

More particularly, hydrophilic bisurethanes useful as the detackifying additive in this invention are compounds selected from the formulas I and II:

R(O)CNH—X—NHC(O)O—Y—O(O)CNH—X—NHC(O)R    (I)

Z—NHC(O)O—Y—O(O)CNH—Z    (II)

where Y is a hydrophilic polymeric chain having a molecular weight in the range of about 1000 to 8000. -O-Y-O can be derived from diols of the general formula (III):

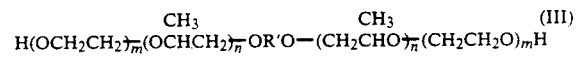

$$H(OCH_2CH_2)_{\overline{m}}(OCHCH_2)_{\overline{n}}OR'O-(CH_2CHO)_{\overline{n}}(CH_2CH_2O)_mH \quad \underset{CH_3}{\overset{CH_3}{|}} \quad (III)$$

where m is an integer of 1 or more and n is 0 or an integer of 1 or more, and R' is $CH_2CH_2$ or $-CH(CH_3)CH_2-$. If n is 0, the compound of formula III is a poly(oxyethylene) diol. The polymer may be a block copolymer or a random copolymer.

Each X in formula I and each Z in formula II may be the same or different and is selected from an aromatic, cycloaliphatic or aliphatic group. In the case of formula I, the bisurethanes are derived from the above described polyetherdiols (III) and diisocyanates which can be either aromatic (e.g., toluene diisocyanate, methylene-4,4'- bis(phenylisocyanate)) or cycloaliphatic (e.g., methylene-4,4'- bis(cyclohexyl)diisocyanate, isophorone diisocyanate, 1,4-cyclohexane diisocyanate) or aliphatic (e.g., hexamethylene diisocyanate), or mixtures thereof. In the case of formula II, the bisurethanes are derived from the above described polyetherdiols (III) and monoisocyanates which can be aromatic (e.g., phenyl isocyanate), cycloaliphatic (cyclohexyl isocyanate) or aliphatic (butyl isocyanate) or mixtures thereof.

In formula I, R is —OR' is where —OR" is derived from monofunctional alcohols such as but not limited to methanol, ethanol, isopropanol, butanol, and lauryl alcohol, or from oxyalkylene adducts of monofunctional alcohols of the general formula IV:

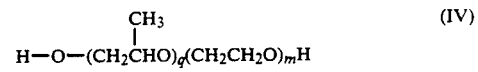

$$H-O-(CH_2CHO)_q(CH_2CH_2O)_mH \quad \underset{CH_3}{\overset{CH_3}{|}} \quad (IV)$$

where q and m are independently 0 or integers of 1 or more, provided that if one of q and m are 0, the other of q and m is an integer of 1 or more. Best results have been attained with bisurethanes of formula I where R is derived from methanol or ethanol.

To prepare the bisurethanes of formula I, one mole of polyether diol is reacted with two moles of diisocyanate to form an isocyanate-terminated prepolymer which is then reacted with two moles of monofunctional alcohol. To prepare the bisurethanes of formula II, one mole of a polyether diol of the general formula III is reacted with two moles of monofunctional isocyanate. The synthesis of the bisurethanes can be carried out in solvent or in bulk. Different types of non-reactive solvents can be used, such as cellosolve acetate and dichloromethane. The reaction temperature is critical in the bisurethane preparation and should not exceed 80 degrees C. because of possible side reactions. The synthesis should be carried out under inert, dry conditions with dried reagents. Small amounts of benzoyl chloride (0.5-1%) can be used in the preparation of the bisurethanes to control the reaction rate.

The preferred bisurethanes for use in this invention are those of Formulas I and II wherein Y is selected from the group consisting of polyethyleneoxides, polypropyleneoxides, and random or block ethylene/propylene oxide copolymers. The most preferred hydrophilic group is a polyethylene glycol having a molecular weight in the range of about 3000 to 5000, most preferably about 4000.

The polyisocyanate prepolymer used in this invention comprises a prepolymer derived from polyisocyanate, preferably aromatic, and a reactive hydrogen compound or oligomer. The preferred prepolymer composition comprises modified diphenylmethane diisocyanate, polypropylene glycol, benzoyl chloride stabilizer and dimorpholinodiethylether catalyst. The preferred isocyanate to diol ratio is about 4 to 1 (NCO/OH =4/1). To prolong the shelf life of the material, certain stabilizers such as benzoyl chloride (0.1 to 1.0 wt. %) may be included in the prepolymer, and foam suppressors such as silicone liquids may also be included.

The advantageous non-tacky yet non-slippery properties of the casting materials of this invention are achieved by blending with the polyisocyanate prepolymer an effective detackifying quantity of a hydrophilic bisurethane as described above. Generally, the hydrophilic bisurethane should be blended with the polyisocyanate prepolymer in the amount of about 0.1 to 10%, preferably 0.5 to 5% and most preferably about 2% per weight of the polyisocyanate prepolymer.

Best results according to this invention have been achieved using a polyisocyanate prepolymer which is the reaction product of 56% diphenylmethane diisocyanate (this and all percentages unless otherwise stated being % by weight of the total reaction products), 37.7% polypropylene glycol (Pluracol P710, BASF Chemicals), 0.1% benzoyl chloride, 2.0% dimorpolinyldiethylether catalyst, 0.2% silicone defoaming agent and 4% of a detackifying mixture prepared by contacting 11% 4,4'-diphenylmethane diisocyanate, 0.5% benzoyl chloride and 8.7% poly(oxyethylene) glycol (MW=4000) which reaction is stopped short by addition of 1.5% ethanol.

The types of fabric upon which a curable polyisocyanate prepolymer is coated or in which such prepolymer may be impregnated have been well described in the art. (E.g., U.S. Pat. No. 4,667,661 and U.S. Pat. No. 4,411,262, the disclosures of which are herein incorporated by reference.) The sheet is semi-rigid or flexible and should be porous so that the curing agent, water, may penetrate into the roll of fabric and contact all parts of the resin. Examples of suitable sheets are woven, non-woven or knit fabrics comprised of natural or synthetic fibers. Preferred sheets are knit fiberglass fabrics, although fabrics of cotton and polyester, for example, may also be used.

The amount of prepolymer/detackifier mixture applied to the fabric must be sufficient for the formation of a strong interlayer laminate bond but not so much as to occlude the porosity and unnecessarily thicken the resin film which should be thin for rapid and complete hardening. Excessive prepolymer may cause the fabric to be messy to handle because of stickiness or dripping and transfer of resin. The desired resin to carrier fabric weight ratio is a function of both the prepolymer viscosity and the surface characteristics of the fabric and is therefore not susceptible to precise quantification; however, an appropriate ratio could be easily determined by one skilled in the art.

The materials of this invention are further illustrated by the following examples, which are intended to be illustrative and not limiting of the scope of this invention.

EXAMPLE 1

Preparation of Nco-Terminated Urethane Prepolymers

Using the following general procedure, the NCO-terminated urethane prepolymers set forth in Table I were prepared.

The polyols utilized were dried at 80° C. under vacuum of 103 mm Hg for 24 hours prior to use.

An NCO-terminated urethane prepolymer was prepared by mixing two (2) equivalents of 4,4'-diphenylmethane diisocyanate ("MDI", Mondur M from Mobay Chemical Corporation) with one (1) equivalent of polyol. The MDI flakes were weighed into a 500 ml reaction kettle equipped with a dropping funnel, a nitrogen inlet and outlet valve, a mechanical stirrer, heating jacket, and thermometer. The MDI was heated to melting at 70° C. under a dry nitrogen blanket. To the melted MDI was added 0.5 percent by weight of the total formulation (MDI +polyol) of benzoyl chloride. The benzoyl chloride was allowed to mix with the MDI at 70° C. until the mixture became homogeneous. The calculated amount of polyol was added to the stirred MDI-benzoyl chloride mixture at 70° C. in a steady stream. The temperature of the reaction was raised above 80° C., depending on the quantity and rate at which the polyol was added. The reaction was controlled using a water bath. Following the addition of the polyol, the temperature should be maintained at 70° C. The reaction was completed in 3-4 hours.

The progress of the reaction was followed by means of the di-n-dibutylamine titration (ASTM D-1638-84). The reaction was considered complete when the determined value of the percent isocyanate in the prepolymer agreed with the theoretical value, calculated based upon the weights of the materials used, within 1%.

TABLE I

| | Composition and Consistency of Bisurethanes | | | |
|---|---|---|---|---|
| | | Component | | |
| Ex. | Polyol, mol | Monofunctional Alcohol, mol | Isocyanate, mol | Consistency |
| 1 | PEG-1000, 1 | EtOH, 2 | MDI, 2 | Solid |
| 2 | PEG-1500, 1 | EtOH, 2 | MDI, 2 | Solid |
| 3 | PEG-4000, 1 | EtOH, 2 | MDI, 2 | Solid |
| 4 | PEG-8000, 1 | EtOH, 2 | MDI, 2 | Solid |
| 5 | PEG-4000, 1 | MeOH, 2 | MDI, 2 | Solid |
| 6 | PEG-4000, 1 | EtOH, 2 | IPDI, 2 | Insoluble gel |
| 7 | PEG-4000, 1 | — | PI, 2 | Solid |
| 8 | PEG-4000, 1 | — | PI, 2 | Solid |
| 9 | — | Polyoxyethylene derivative of nonyl phenol, | MDI, 1 | Liquid |

TABLE I-continued

Composition and Consistency of Bisurethanes

| Ex. | Polyol, mol | Monofunctional Alcohol, mol | Isocyanate, mol | Consistency |
|---|---|---|---|---|
| | | MW 632 | | |

PEG-1000 = Poly-G-1000, Olin Chemical
PEG-1500 = Poly-G-1500, Olin Chemical
PEG-4000 = Pluracol E-4000, BASF Chemicals
PEG-8000 = Pluracol E-8000, BASF Chemicals
Polyoxyethylene derivative of nonyl phenol = Surfonic N-95, Texaco Chemicals
MDI = 4,4'-diphenylmethane diisocyanate, Mondur M, Mobay Chemicals
IPDI = isophorone diisocyanate, "IPDI" from Huels America
PI = phenyl isocyanate, "PI" from Aldrich Chemicals

Preparation of Bis-Urethane

An equivalent amount of 100% ethanol was added to the stirred urethane prepolymer at 70° C. under nitrogen in an excess of 2-3$. The kettle was equipped with a water-cooled condenser to prevent evaporation of the alcohol. The alcohol, at room temperature, was added in one portion to the stirred prepolymer by means of a dropping funnel. The reaction between the NCO-prepolymer and the alcohol occurred very quickly at 70° C. and the reaction was completed in two hours. The reaction was again followed by the n-dibutyl amine titration and was considered complete when the percent isocyanate in the material was zero. The bis-urethane material was then transferred and stored in a closed glass bottle or metal can.

The bisurethanes prepared as described above were blended with polyisocyanate prepolymer (reaction product of diphenylmethane diisocyanate and polypropylene glycol) at room temperature. Bisurethanes which were solid at room temperature were melted at 70°-80° C. prior to mixing. After standing for twenty-four hours at room temperature, the resulting mixtures were tested for compatibility, viscosity, isocyanate concentration, and tackiness and slip properties.

Tackiness and slip properties were measured according to the following procedure: A tape is coated with the polyisocyanate prepolymer/bisurethane mixture. The coated tape is dipped in water five times. Slip properties are measured by noting the relative slipperiness of rubber gloves to the coated surface.

The test method for determining tackiness is a qualitative test. The resin mixture is applied to four inches of a 1"×5" long tape, leaving one inch of the tape dry. The coated tape is dipped in water, laid flat, and a 1"×4" piece of a rubber glove is firmly pressed to it. One inch of the uncoated portion of the tape is clamped to the ring portion of a ring stand using a clothespin. Afterwards, a five gram weight on a string is attached to the tape using a paper clip to the rubber glove portion ⅛ inch from the edge. The released weight is allowed to pull the rubber from the tape. The time necessary to completely pull the four inch strip of rubber from the tape is measured using a stopwatch.

The properties of the resulting casting resins are set forth in Table II.

TABLE II

| Example | Concentration Bisurethane, % | Viscosity, cps | Peel time sec. | % NCO |
|---|---|---|---|---|
| Control | 0 | 13,400 | 15 | 11.27 |
| 1 | 2 | 12,800 | 8 | 9.60 |
| 2 | 2 | 11,400 | 5 | 10.31 |
| 3 | 2 | 17,400 | 6 | 10.33 |
| 4 | 2 | 102,600 | v. long | 9.92 |
| 5 | 2 | 23,400 | 12 | 10.02 |
| 6 | — | — | — | — |
| 7 | 2 | 13,400 | 3.5 | 10.78 |
| 8 | 2 | 20,600 | 2.2 | 8.59 |
| 9 | 2 | 22,200 | 7.0 | 8.75 |

What is claimed is:

1. An orthopedic casting material comprising a fabric coated or impregnated with a combination of a reactive fluid water-curable polyisocyanate prepolymer and an effective detackifying quantity of one or more hydrophilic bisurethanes selected from the group consisting of compounds of the formulas I and II:

$$R(O)CNH-X-NHC(O)O-Y-O(O)CNH-X-NHC(O)R \quad (I)$$

$$Z-NHC(O)O-Y-O(O)CNH-Z \quad (II)$$

where Y is a hydrophilic polymeric chain having a molecular weight in the range of about 1000 to 8000; each X in formula I and each Z in formula II may be the same or different and is selected from aromatic, cycloaliphatic or aliphatic groups; and R is derived from monofunctional C1-C6 alcohols or from oxyalkylene adducts of monofunctional alcohols of the general formula IV:

$$H-O-(CH_2CHO)_q(CH_2CH_2O)_mH \quad (IV)$$
$$\phantom{H-O-(}|\phantom{CH_2CHO)_q(CH_2CH_2O)_mH}$$
$$\phantom{H-O-(CH_2}CH_3$$

where q and m are independently 0 or a positive integer, provided that if one of q or m is 0, the other of q or m is a positive integer.

2. The casting material of claim 1 wherein -O-Y-O is derived from diols of the general formula (III):

$$H(OCH_2CH_2)_m(OCHCH_2)_nOR'O-(CH_2CHO)_n(CH_2CH_2O)_mH \quad (III)$$
$$\phantom{H(OCH_2CH_2)_m(O}|\phantom{CHCH_2)_nOR'O-(CH_2}|\phantom{CHO)_n(CH_2CH_2O)_mH}$$
$$\phantom{H(OCH_2CH_2)_m(O}CH_3\phantom{CH_2)_nOR'O-(CH_2}CH_3$$

where m and n are independently 0 or a positive integer and R is $CH_2CH_2$ or $-CH(CH_3)CH_2-$.

3. The casting material of claim 1 wherein the diol is a polyethylene glycol and has a molecular weight in the range of about 3000 to 5000.

4. The casting material of claim 3 wherein the polyethylene glycol has a molecular weight of about 4000.

5. The casting material of claim 1 wherein the bisurethane has the formula I.

6. The casting material of claim 1 wherein the bisurethane has the formula II.

7. The casting material of claim 5 wherein (O)CNH-X-NHC(O) is derived from a diisocyanate selected from the group consisting of toluene diisocyanate, methylene-4,4'-bis(phenylisocyanate), methylene-4,4'-bis(cyclohexyl)diisocyanate, isophorone diisocyanate, 1,4-cyclohexane diisocyanate, hexamethylene diisocyanate), and mixtures thereof.

8. The casting material of claim 6 wherein Z-NHC(O) and (O)CNH-Z are derived from a monoisocyanate selected from the group consisting of phenyl isocyanate, cyclohexyl isocyanate, butyl isocyanate and mixtures thereof.

9. The casting material of claim 5 where R is derived from methanol or ethanol.

10. The casting material of claim 5 where O—Y—O— is derived from a polyethylene glycol having a molecular weight in the range of about 3000 to 5000, X is derived from methylene-4,4'-bis(phenylisocyanate), and R is derived from ethanol.

11. The casting material of claim 10 where —O—Y—O— is derived from polyethylene glycol having a molecular weight of about 4000.

12. The casting material of claim 6 where O—Y—O is derived from a polyethylene glycol having a molecular weight in the range of about 3000 to 5000.

13. The casting material of claim 12 where —O—Y—O— is derived from a polyethylene glycol having a molecular weight of about 4000.

14. The casting material of claim 1 where said hydrophilic bisurethane is blended with said polyisocyanate prepolymer in a quantity of about 0.5 to 5 weight % based on the weight of said prepolymer.

15. The casting material of claim 1 in which said fabric is a knit fiberglass fabric.

16. The casting material of claim 1 in which said polyisocyanate prepolymer comprises the reaction product of diphenylmethane diisocyanate and polypropylene glycol.

17. A prepolymer mixture for use in orthopedic casting materials comprising a polyisocyanate prepolymer and an effective detackifying quantity of one or more hydrophilic bisurethanes selected from the group consisting of compounds of formulas I and II:

$$R(O)CNH-X-NHC(O)O-Y-O(O)CNH-X-NHC(O)R \quad (I)$$

$$Z-NHC(O)O-Y-O(O)CNH-Z \quad (II)$$

where Y is a hydrophilic polymeric chain having a molecular weight in the range of about 1000 to 8000; each X in formula I and each Z in formula II may be the same or different and is selected from aromatic, cycloaliphatic or aliphatic groups; and R is derived from monofunctional C1-C6 alcohols or from oxyalkylene adducts of monofunctional alcohols of the general formula IV:

$$H-O-(CH_2\overset{\underset{\displaystyle CH_3}{|}}{C}HO)_q(CH_2CH_2O)_mH \quad (IV)$$

where q and m or independently 0 or a positive integer, provided that if one of q or m is 0, the other of q or m is a positive integer.

* * * * *

UNITED STATES PATENT AND TRADEMARK OFFICE
CERTIFICATE OF CORRECTION

PATENT NO. : 5,180,632
DATED : January 19, 1993
INVENTOR(S) : EDENBAUM ET AL.

It is certified that error appears in the above-identified patent and that said Letters Patent is hereby corrected as shown below:

Column 2, Line 24 delete "is $CH_2CH_2$ or" and insert therefor --is $-CH_2CH_2-$ or--.

Column 2, Line 43 delete "-OR' is where -OR" is"

Column 4, Line 42 delete "The di-n-dibutylamine" and insert therefor --The di-n-butylamine--.

Column 6, Line 47 delete "is $CH_2CH_2$ or" and insert therefor --is $-CH_2CH_2-$ or--.

Column 7, Lines 3-4 delete " where O-Y-O- is" and insert therefor --where -O-Y-O- is--.

Column 7, Line 11 delete "where O-Y-O is" and insert therefor --where -O-Y-O- is--.

Signed and Sealed this

Fourth Day of January, 1994

Attest:

BRUCE LEHMAN

Attesting Officer

Commissioner of Patents and Trademarks